United States Patent [19]
Tsai et al.

[11] Patent Number: 6,010,975
[45] Date of Patent: Jan. 4, 2000

[54] CATALYST COMPOSITION FOR PREPARING 3-PENTENOIC ESTER FROM BUTADIENE

[75] Inventors: Jing-Cherng Tsai, Kaohsiung; Wen-Sheng Chang, Miaoli Hsien; Chen-Pang Liu, Hsinchu; Jui-Hsien Huang, Changhua Hsien; Bor-Ping Wang, Taoyuan, all of Taiwan

[73] Assignee: Industrial Technology Research Institute, Hsinchu, Taiwan

[21] Appl. No.: 09/100,844

[22] Filed: Jun. 19, 1998

[51] Int. Cl.$^7$ .............................. B01J 31/18; B01J 31/24; B01J 31/04; B01J 31/28

[52] U.S. Cl. .................... 502/155; 502/154; 502/162; 502/167; 502/170; 502/208; 502/213; 502/326

[58] Field of Search ...................... 502/155, 154, 502/162, 167, 170, 208, 213, 326

[56] References Cited

U.S. PATENT DOCUMENTS

| | | | |
|---|---|---|---|
| 4,824,817 | 4/1989 | Drent | 502/154 |
| 5,028,734 | 7/1991 | Drent | 560/207 |
| 5,495,041 | 2/1996 | Sielcken et al. | 560/207 |
| 5,679,831 | 10/1997 | Sielcken | 560/204 |

*Primary Examiner*—Elizabeth D. Wood
*Attorney, Agent, or Firm*—W. Wayne Liauh

[57] ABSTRACT

A catalyst composition for the preparation of 3-pentenoic ester from butadiene. The catalyst composition includes a palladium complex; and a bidentate phosphine with the following formula: $_1R_2P-(CH_2)n-PR_3R_4$, wherein n is a integer from 1 to 6; and a bulky benzoic carboxylic acid.

12 Claims, No Drawings

CATALYST COMPOSITION FOR PREPARING 3-PENTENOIC ESTER FROM BUTADIENE

FIELD OF THE INVENTION

The present invention relates to a catalyst composition for preparing 3-pentenoic ester from butadiene. More specially, the invention relates to a catalyst composition which allows hydrocarbonylation of butadiene in the presence of carbon monoxide and an alcohol.

BACKGROUND OF THE INVENTION

The hydrocarbonylation of butadiene to obtain 3-pentenoic ester is a valuable process since 3-pentenoic ester is the starting material for the preparation of 5-formylvalerate esters, which are important intermediates for the preparation of caprolactam. Processes for preparing 3-pentenoic ester from hydrocarbonylation of butadiene are disclosed in U.S. Pat. No. 5,028,734 and U.S. Pat. No. 5,495,041. Both processes involve using butadiene to undergo the hydrocarbonylation reaction, providing 3-pentenoic ester as the major product. The catalyst for the hydrocarbonylation of butadiene disclosed in U.S. Pat. No. 5,028,734 is composed of a palladium complex, bidentate phosphine ligands and a benzoic carboxylic acid. The catalyst composition converts 75% of the butadiene to 3-pentenoic ester. The disadvantage of the catalyst is that another side reaction product, 2-pentenoic ester, is produced in addition to the 3-pentenoic ester in the reaction mixture. Thereby, the selectivity for 3-pentenoic ester using this catalyst composition is low. The other disadvantage of the invention is that the catalyst composition comprises benzoic acid, which can easily undergo esterfication in the presence of alcohols, thereby necessitating a constant feeding of the benzoic acid into the catalyst system to maintain efficient reactivity. Moreover, the co-catalyst can not be reused before hydrolysis and recovery. The hydrocarbonylation catalyst disclosed in U.S. Pat. No. 5,495,041 is composed of a palladium complex, bindenate phosphine ligands and 3-pentenoic acid. The drawback of this invention is that the conversion rate of butadiene is about 80%; however, the selectivity of 3-pentenoic ester is less than 50%. Therefore, the yield of 3-pentenoic esters according to the invention is too low.

Both catalyst systems suffer from the disadvantage of that either extra benzoic acid must be constantly fed into the catalyst system to maintain sufficient catalytic activity or the selectivity of 3-pentenoic esters is low. Consequently, it is necessary to develop a catalyst composition which converts butadiene to give 3-pentenoic ester with high selectivity and which undergos hydrocarbonylation reaction without the requirement of constant feeding of co-catalyst.

SUMMARY OF THE INVENTION

It is therefore an object of the invention to develop a catalyst composition for preparing 3-pentenoic ester with high selectivity. More specially, the object of the invention is to develop a catalyst composition containing a bulky co-catalyst, which allow hydrocarbonylation to take place in the presence of carbon monoxide and an alkyl alcohol.

The catalyst composition disclosed in the present invention comprises the following components:

(a) 0.1 to 10 parts by mole of a palladium complex;

(b) 0.6 to 60 parts by mole of a bidentate phosphine ligand;

(c) 1.0 to 100 parts by mole of a bulky benzoic carboxylic acid.

wherein the palladium complex is selected from the group consisting of palladium acetate, palladium acetylacetonate, or palladium hexafluoroacetylacetoneate; and the bidentate phosphine ligand can be expressed by the following formula: $R_1R_2P-(CH_2)n-PR_3R_4$, wherein n is a integer from 1 to 6, and $R_1$, $R_2$, $R_3$, $R_4$ can be independent phenyl, naphthyl, or aromatic compounds with fused ring structures. According to this invention, the ligands can be selected from $\alpha,\alpha'$-diphenyl phosphino-o-xylene or 2,2'-bis (diphenylphosphino methyl)-1,1'-biphenyl; the bulky benzoic carboxylic acid is selected from the group consisting of 2,4,6-tri-isopropyl benzoic acid, 2,4,6-tri-tert-butyl benzoic acid, 2,4,6-tri-isobutyl benzoic acid, 2,6-di-isopropyl benzoic acid, 2,6-tri-tert-butyl benzoic acid and 2,6-di-isobutyl benzoic acid.

The improved catalyst composition disclosed in the present invention can be used in the presence of carbon monoxide and an alkyl alcohol for hydrocarbonylation of butadiene to provide 3-pentenoic esters with high selectivity and good yield.

One of the advantage of the catalyst composition disclosed in the present invention is that the selectivity of 3-pentenoic ester is high, thereby providing 3-pentenoic ester with good yield.

Another advantage of the catalyst composition disclosed in the present invention is that bulky benzoic acid derivatives which can not undergo esterfication in the presence of alkyl alcohols are used as the co-catalyst instead of conventional benzoic acid. Therefore, the undesired esterification of co-catalyst can be prevented, and supplemental amounts of co-catalyst are not needed.

DETAILED DESCRIPTION OF THE PREFERRED EMBODIMENTS

The present invention discloses a catalyst composition for hydrocarbonylation of butadiene to give 3-pentenoic ester. The catalyst composition disclosed in the present invention allows the reaction to take place in the presence of carbon monoxide and a bulky carboxylic acid to give 3-pentenoic ester with high selectivity and provides a novel process of preparing 3-pentenoic ester that does not require supplemental amounts of co-catalyst.

The catalyst composition disclosed in the present invention comprises the following components:

(a) a palladium complex;

(b) a bidentate phosphine ligand with a formula as $R_1R_2P-(CH_2)_n-PR_3R_4$; and (c) a bulky benzoic carboxylic acid.

wherein the palladium complex is selected from the group consisting of palladium acetate, palladium acetylacetonate, or palladium hexafluoroacetylacetoneate, and the amount of the palladium complex is about 0.1 to 10 parts by mole; the bidentate phosphine ligand is selected from the group consisting of $\alpha,\alpha'$-diphenyl phosphino-o-xylene and 2,2'-bis (diphenylphosphino methyl)-1,1'-biphenyl, and the amount of the bidentate phosphino ligand is about 0.6 to 60 parts by mole; the bulky benzoic carboxylic acid is selected from the group consisting of 2,4,6-tri-isopropyl benzoic acid, 2,4,6-tri-tert-butyl benzoic acid, 2,4,6-tri-isobutyl benzoic acid, 2,6-di-isopropyl benzoic acid, 2,6-tri-tert-butyl benzoic acid and 2,6-di-isobutyl benzoic acid, and the amount of the bulky benzoic acid is about 1.0 to 100 parts by mole.

The hydrocarbonylation process related to present invention can be conducted in a high-boiling inert solvent, such as $C_7$–$C_{20}$ alkanes, arylalkanes or aryl ethers, thereby allowing the desired reaction product, 3-pentenoic ester, to be removed from the reaction mixture by distillation. The remaining catalyst components can be reused by feeding in another portion of the butadiene and charging the solution with carbon monoxide and alcohols for hydrocarbonylation.

The present invention will now be described more specifically with reference to the following examples. It is to be noted that the following descriptions of examples, including the preferred embodiment of this invention, are presented herein for purposes of illustration and description, and are not intended to be exhaustive or to limit the invention to the precise form disclosed.

EMBODIMENT

EXAMPLE 1

A 150 ml autoclave was dried under vacuum and was refilled with nitrogen. The reactor was then consecutively charged with 0.06 g (0.27 mmol) of palladium acetate, 0.51 g (1.08 mmol) of α,α'-diphenyl phosphino-o-xylene, 50 ml of diphenyl methane (as inert solvent), 2.1 g (65.63 mmol) of methanol and 5 ml of butadiene (57.3 mmol). The catalyst composition also contained a bulky benzoic carboxylic acid selected from the group consisting of 2,4,6-tri-isopropyl benzoic acid, 2,4,6-tri-tert-butyl benzoic acid, 2,4,6-tri-isobutyl benzoic acid, 2,6-di-isopropyl benzoic acid, 2,6-tri-tert-butyl benzoic acid, and 2,6-di-isobutyl benzoic acid. The resulting autoclave was allowed to heat to 150° C. and was then charged with 60 atm of carbon dioxide to start the reaction. The reaction was maintained at 150° C. under 60 atm of carbon monoxide for three hours. Then, the autoclave was allowed to cool to room temperature. Analysis of the reaction mixture indicated that the conversion of butadiene was 92%, the selectivity for the desired 3-pentenoic ester was 93%, and the selectivity for 2-pentenoic ester was 3.5%.

EXAMPLE 2

The reaction solution in example 1 was allowed to undergo vacuum distillation to remove volatiles and reaction products from the reactor. The distillation provided the desired reaction products, including approximately 94% 3-pentenoic ester and 3% 2-pentenoic ester as well as 3% butadiene dimers. In order to examine the stability of the catalyst system, the reactor was refilled with 2.1 g of methanol, and 5 ml of butadiene and was again allowed to repeat the carbonylation reaction. After maintaining the reaction at 150° C. and under 60 atm of carbon monoxide for three hours, the reactor was cooled to room temperature. Analysis of the reaction solution indicated that the catalytic reactivity and selectivity remained constant for the repeated reaction.

EXAMPLE 3

The reaction in Example 2 was repeated 8 times to demonstrate the stability of the catalyst system. A summary of the results is presented in Table 1.

TABLE 1

| Reaction No. | Conversion percentage of butadiene | Selectivity for 3-pentenoic ester | Selectivity for 2-pentenoic ester |
|---|---|---|---|
| 1 | 92% | 93% | 3.0% |
| 2 | 94% | 93% | 3.6% |
| 3 | 90% | 94% | 4.1% |

TABLE 1-continued

| Reaction No. | Conversion percentage of butadiene | Selectivity for 3-pentenoic ester | Selectivity for 2-pentenoic ester |
|---|---|---|---|
| 4 | 90% | 93% | 3.1% |
| 5 | 90% | 92% | 3.5% |
| 6 | 91% | 93% | 3.4% |
| 7 | 89% | 92% | 3.2% |
| 8 | 88% | 93% | 3.5% |

Comparative Example 1

Example 1 was repeated except with that 0.43 g of 1,4-diphenyl phosphinobutane (1.08 mmol) was used instead of α,α'-diphenyl phosphino-o-xylene, and 0.31 g (1.89 mmol) of 2,4,6-trimethyl benzoic acid was used instead of 2,4,6-triisopropyl benzoic acid. The reaction was again maintained at 150° C. under 60 atm of carbon monoxide for three hours. Analysis of the reaction solution indicated that the conversion of butadiene was 94%, the selectivity for the desired 3-pentenoic ester was 68%, and the selectivity for 2-pentenoic ester was 23%.

Comparative Example 2

The reaction solution in the comparative example 1 was allowed to undergo vacuum distillation to remove volatiles and reaction products from the reactor. In order to examine the stability of the catalyst system, the reactor was refilled with 2.1 g of methanol, and 5 ml of butadiene and was again allowed to repeat the carbonylation reaction. After maintaining the reaction at 150° C. under 60 atm of carbon monoxide for three hours, the reactor was cooled to room temperature. Analysis of the reaction solution indicated the conversion of butadiene was 85%, the selectivity for the desired 3-pentenoic ester was 65%, and the selectivity for 2-pentenoic ester was 19%. The GC analysis also indicated the formation of 2,4,6-trimethyl benzoic methyl ester (derived from the esterification of the 2,4,6-trimethyl benzoic acid). Through this, the total amount of benzoic acid decreased during the reaction. Consequently, a decrease in the carbonylation reaction rate was observed.

Compared with the conventional catalyst systems described above for hydrocarbonylation of butadiene with a selectivity of pentenoic ester less than 84%, the selectivity of 3-pentenoic ester by using the catalyst of this present invention is greater than 92.7%, and the selectivity of 2-pentenoic ester is only about 3.4%. Moreover, the esterification ratio of co-catalyst in the reaction medium is inhibited; thus no extra supply of co-catalyst is required.

What is claimed is:

1. A catalyst composition for preparing a 3-pentenoic ester from butadiene and an alcohol, comprising:
   (a) a palladium complex;
   (b) a bidentate phosphine ligand with the following formula:

$R_1R_2P$—$(CH_2)_n$—$PR_3R_4$;

wherein n is an integer from 1 to 6, $R_1$, $R_2$, $R_3$, $R_4$, are, independently phenyl, naphenyl, or aromatic fused ring substituants, and
   (c) a bulky benzoic carboxylic acid, selected from the group consisting of 2,4,6-tri-isopropyl benzoic acid, 2,4,6-tri-tert-butyl benzoic acid, 2,4,6-tri-isobutyl benzoic acid, 2,6-di-isopropyl benzoic acid, 2,6-tri-tert-butyl benzoic acid, and 2,6-di-isobutyl benzoic acid.

2. The catalyst composition as claimed in claim 1, wherein the palladium complex is selected from the group consisting of palladium acetate, palladium acetylacetonate, and palladium hexafluoroacetylacetoneate.

3. The catalyst composition as claimed in claim 1, wherein the amount of the palladium complex is about 0.1 to 10 parts by mole.

4. The catalyst composition as claimed in claim 1, wherein the amount of the bidentate phosphine ligand is about 0.6 to 60 parts by mole.

5. The catalyst composition as claimed in claim 1, wherein the bulky benzoic carboxylic acid is selected from the group consisting of 2,4,6-tri-isopropyl benzoic acid, 2,4,6-tri-tert-butyl benzoic acid, 2,4,6-tri-isobutyl benzoic acid, 2,6-di-isopropyl benzoic acid, 2,6-tri-tert-butyl benzoic acid and 2,6-di-isobutyl benzoic acid.

6. The catalyst composition as claimed in claim 1, wherein the amount of the bulky benzoic carboxylic acid is about 1.0 to 100 parts by mole.

7. A catalyst composition for preparing a 3-pentenoic ester from butadiene and an alcohol, comprising:

(a) a palladium complex;

(b) a bidentate phosphine ligand with the following formula:

$R_1R_2P-(CH_2)_n-PR_3R_4;$ wherein n is an integer from 1 to 6, $R_1$, $R_2$, $R_3$, $R_4$, are, independently, phenyl, naphenyl, or aromatic fused ring substituants; and (c) wherein said bidentate phosphine ligand is selected from the group consisting of α,α'-diphenyl phosphino-o-xylene and 2,2'-bis(diphenylphosphino methyl)-1,1'-biphenyl.

8. A catalyst composition as claimed in claim 7, wherein the palladium complex is selected from the group consisting of palladium acetate, palladium acetylacetonate, and palladium hexafluoroacetylacetonate.

9. A catalyst composition as claimed in claim 7, wherein the amount of the palladium complex is about 0.1 to 10 parts by mole.

10. A catalyst composition as claimed in claim 7, wherein the amount of the bidentate phosphine ligand is about 0.6 to 60 parts by mole.

11. A catalyst composition as claimed in claim 7, which further comprises a bulky benzoic carboxylic acid selected from the group consisting of 2,4,6-tri-isopropyl benzoic acid, 2,4,6-tri-tert-butyl benzoic acid, 2,4,6-tri-isobutyl benzoic acid, 2,6-di-isopropyl benzoic acid, 2,6-tri-tert-butyl benzoic acid, and 2,6-di-isobutyl benzoic acid.

12. A catalyst composition as claimed in claim 11, wherein the amount of the bulky benzoic carboxylic acid is about 1.0 to 100 parts by mole.

* * * * *